United States Patent [19]

Sigwart et al.

[11] Patent Number: 5,929,261
[45] Date of Patent: Jul. 27, 1999

[54] PROCESS FOR THE SELECTIVE HYDRATION OF VINYLOXIRANE TO 1,2-BUTYLENE OXIDE OF HETEROGENEOUS CATALYSTS

[75] Inventors: Christoph Sigwart, Schriesheim; Daniel Heineke, Ludwigshafen; Klemens Flick, Herxheim, all of Germany

[73] Assignee: BASF Aktiengesellschaft, Ludwigshafen, Germany

[21] Appl. No.: 09/101,686

[22] PCT Filed: Jan. 22, 1997

[86] PCT No.: PCT/EP97/00281

§ 371 Date: Jul. 15, 1998

§ 102(e) Date: Jul. 15, 1998

[87] PCT Pub. No.: WO97/27182

PCT Pub. Date: Jul. 31, 1997

[30] Foreign Application Priority Data

Jan. 26, 1996 [DE] Germany .......................... 196 02 710

[51] Int. Cl.$^6$ .................................................. C07D 301/02
[52] U.S. Cl. .............................................................. 549/540
[58] Field of Search ............................................... 549/540

[56] References Cited

U.S. PATENT DOCUMENTS

| | | | |
|---|---|---|---|
| 2,561,984 | 7/1951 | Hillyer et al. .......................... | 260/598 |
| 4,897,489 | 1/1990 | Monnier et al. ........................ | 549/534 |
| 5,077,418 | 12/1991 | Falling .................................... | 549/540 |
| 5,117,013 | 5/1992 | Falling .................................... | 549/54 |
| 5,516,851 | 5/1996 | Flick et al. ........................... | 525/330.2 |

FOREIGN PATENT DOCUMENTS

| | | |
|---|---|---|
| 653 243 | 5/1995 | European Pat. Off. . |
| 724 907 | 8/1996 | European Pat. Off. . |
| 44 07 486 | 9/1995 | Germany . |
| 44 22 046 | 1/1996 | Germany . |
| 19532 645 | 3/1997 | Germany . |

OTHER PUBLICATIONS

Petroleum Chem. Neftekhimiya, vol. 33, 1993, 120–127.

Angew. Chem. Int. Ed. Engl. 30 (1991), No. 10, Boennemann et al., 1312–1314.

Jrl. Gen. Chem. USSR, vol. 28, No. 9, Sep. 1958, Aizikovich et al., 3076–3080.

*Primary Examiner*—Ba K. Trinh
*Attorney, Agent, or Firm*—Keil & Weinkauf

[57] ABSTRACT

A process for preparing 1,2-butylene oxide by catalytic hydrogenation of vinyloxirane over a heterogeneous catalyst comprises using a catalyst prepared by applying at least one element of groups 7 to 11 of the Periodic Table in the form of a sol to an inert support.

4 Claims, No Drawings

PROCESS FOR THE SELECTIVE HYDRATION OF VINYLOXIRANE TO 1,2-BUTYLENE OXIDE OF HETEROGENEOUS CATALYSTS

This is a 371 application of PCT/EP07/00281, dated Jan. 22, 1997.

The present invention relates to an improved process for preparing 1,2-butylene oxide by catalytic hydrogenation of vinyloxirane over heterogeneous catalysts.

The hydrogenation of vinyloxirane by heterogeneous catalysis is known.

According to U.S. Pat. No. 2,561,984, the hydrogenation of vinyloxirane in ethanol over a palladium on activated carbon catalyst at 25° C./2 bar gives n-butyraldehyde as main product after a reaction time of 3 h. By contrast, Raney nickel catalyst at 25° C. and 2 bar chiefly produces n-butanol after a reaction time of 1.5 h. Nothing is reported about the formation of 1,2-butylene oxide.

A paper by Aizikovich et al. (J. Gen. Chem. USSR, 28 (1958) 3076) describes the catalytic hydrogenation of vinyloxirane in methanol or ethanol over platinum, palladium and Raney nickel catalysts. A supported palladium catalyst (1.8% by weight of palladium on calcium carbonate) at 15° C./1 bar results mainly in the formation of n-butanol. Crotyl alcohol is reported as the most important intermediate compound of the hydrogenation, although the formation of n-butyraldehyde is observed as well. Again there is no mention of the formation of 1,2-butylene oxide.

In U.S. Pat. No. 5,077,418 and U.S. Pat. No. 5,117,013 it is reported that the hydrogenation of vinyloxirane solutions over palladium-containing catalysts gives n-butyraldehyde as main product. For instance, hydrogenation of vinyloxirane together with tetrahydrofuran as solvent over a supported palladium catalyst (5% by weight of palladium on activated carbon) at a temperature of from 50 to 55° C. and a pressure of 3.5 bar gives after a reaction time of 3 h a hydrogenation effluent comprising 55% of n-butyraldehyde, only 27% of 1,2-butylene oxide and 9% of n-butanol. If the hydrogenation is carried out over alumina-supported palladium catalysts (5% of $Pd/Al_2O_3$), only traces of 1,2-butylene oxide are formed after 6 hours at from 25 to 55° C. and a pressure of 3.5 bar or after 4 hours at 100° C. and 20.7 bar. n-Butyraldehyde is formed as the main product with a selectivity of, respectively, 87% or 78% and quantitative conversion. The two U.S. applications also describe the hydrogenation of vinyloxirane over Raney nickel, when n-butanol is formed as the main product. The 1,2-butylene oxide yield is relatively low at 41%. The hydrogenation of vinyloxirane over a supported platinum catalyst (1% by weight of $Pt/Al_2O_3$) at 100° C. and 20.7 bar hydrogen pressure produces after 4.6 h and complete conversion only 40% of 1,2-butylene oxide and also 23% of n-butanol, 24% of butanols, 5% of crotonaldehyde and 3% of n-butyraldehyde. Other platinum catalysts give even lower 1,2-butylene oxide yields.

U.S. Pat. No. 5,077,418 and U.S. Pat. No. 5,117,013 further teach that high 1,2-butylene oxide yields are obtained only with rhodium catalysts. The hydrogenation of vinyloxirane solutions with various supported rhodium catalysts (5% by weight of rhodium on activated carbon, 5% by weight of rhodium on alumina) which, however, have a high content of the costly noble metal rhodium, or hydrated rhodium oxide ($Rh_2O_3 * xH_2O$) gives 1,2-butylene oxide contents of 60 to 93%. The disadvantage of this process is the low space-time yield based on the rhodium used. For instance, the space-time yield in Example 2 of U.S. Pat. No. 5,117,013 is only 110 kg of 1,2-butylene oxide/kg of Rh * h.

Neftekhimiya 33 (1993) 131 describes the hydrogenation of vinyloxirane over nickel, palladium and copper catalysts. Using Raney nickel or nickel on kieselguhr as catalyst, the hydrogenation proceeds mainly with cleavage of the epoxide ring, which leads to predominant formation of 1-butenols and n-butanol. The yields of butylene oxide are low. For instance, a hydrogenation trial in methanol at 20° C./60 bar hydrogen pressure over a Raney nickel catalyst pretreated with isopropanol, nicotinic acid, pyridine and morpholine gave a butylene oxide selectivity of only 37% at 89% conversion. Palladium catalysts, it is true, give higher butylene oxide selectivities compared with nickel catalysts. For example, after 13 min reaction at 15° C./60 bar hydrogen pressure without a solvent, a palladium/activated carbon catalyst yields 81% of butylene oxide based on converted vinyloxirane, at a conversion of 61%. Since vinyloxirane and 1,2-butylene oxide are virtually impossible to separate by distillation, however, this process has no industrial relevance. Copper catalysts have a lower hydrogenation activity and lead to an industrially impracticable resinification of the hydrogenation effluent.

German Patent Application P 44 22 046.4 relates to palladium catalysts produced by impregnating certain support materials with metal salts ($Pd/BaSO_4$, $Pd/ZrO_2$, $Pd/TiO_2$, Pd/Re/support) for use in the selective hydrogenation of vinyloxirane to 1,2-butylene oxide. Despite the high butylene oxide selectivities described in this reference, relatively large amounts of butyraldehyde are formed as byproduct (4–20%). DE-A 44 07 486 teaches the hydrogenation of vinyloxirane over catalysts obtained by vapor deposition of the catalytically active elements on a support of metal foil or metal wire wovens. These catalysts make possible a highly selective conversion to the desired product (1,2-butylene oxide yield: 75–90%), but the metal supports used are relatively costly.

German Patent Application 19 532 645.8 relates to the catalytic hydrogenation of vinyloxirane over heterogeneous catalysts prepared by gas phase deposition of elements of groups 7 to 11 of the Periodic Table on an inert, nonmetallic support.

It is an object of the present invention to provide a more economical process for preparing 1,2-butylene oxide from vinyl-oxirane whereby 1,2-butylene oxide is formed in high yield and selectivity and for which the hydrogenation catalysts used are inexpensive to make, especially through the use of inexpensive support materials, through simple application of the active component and through the use of small amounts of active component.

We have found that this object is achieved by a process for preparing 1,2-butylene oxide by catalytic hydrogenation of vinyl-oxirane over a heterogeneous catalyst, which comprises using a catalyst prepared by applying at least one element of groups 7 to 11 of the Periodic Table in the form of a sol to an inert support.

The process of the invention makes it possible to hydrogenate the double bond of vinyloxirane (I) selectively according to equation (1)

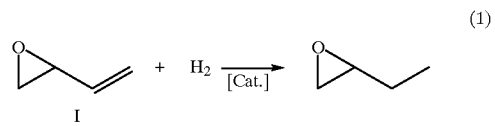

(1)

without the sensitive epoxide ring being hydrogenolytically cleaved to any appreciable extent during the hydrogenation and without appreciable occurrence of other secondary reactions, for example isomerization of the vinyloxirane, for example to crotonaldehyde which is subsequently hydrogenated to crotyl alcohol and butanol. When rhodium catalysts are used, higher productivities based on noble metal used can be achieved compared with the rhodium catalysts described in U.S. Pat. No. 5,077,418 and U.S. Pat. No. 5,117,013.

The catalysts used according to the invention are prepared by applying elements of groups 7 to 11 of the Periodic Table, preferably Re, Ru, Co, Rh, Ir, Ni, Pd, Pt, Cu, Ag, Au, in particular Re, Ru, Rh, Pd and Pt, as sol to an inert support. The catalysts of the invention include one or more of the metals mentioned.

The catalysts of the invention preferably have a metal content of from 0.001 to 2% by weight, advantageously from 0.005 to 0.5% by weight, in particular from 0.005 to 0.1% by weight, based on the catalyst. The catalyst is prepared by spraying a hot support, or by impregnating the support, with a previously prepared sol. The metal sol is a colloidal substance and can be prepared according to known methods, for example from metal salts in which the metal is present in an oxidation state greater than zero. It is possible to use aqueous solutions of the chlorides, acetates or nitrates of the metal, for example. However, other metal salts are usable as well; there is no restriction as regards the anion. Suitable reducing agents include organic compounds such as ethanol, methanol, carboxylic acids and their alkali metal salts and also inorganic compounds such as $N_2H_4$ or $NaBH_4$. Preference is given to hydrazine $N_2H_4$ and ethanol. The size of the metal particles in the sol depends on the strength of the reducing agent used and on the metal salt used. The sols can be stabilized by addition of organic polymers such as polyamines, polyvinylpyrrolidone or polyacrylates, in which case polyvinylpyrrolidone PVP is preferred. However, the sols can also be prepared according to other procedures described in the literature. Bödnnemann et al. (Angew. Chemie, 103 (1991) 1334), for example, describe the preparation of stable metal sols by reduction of metal salts with $(C_8H_{17})_4N[BEtH_3]$.

Suitable inert support substances for the catalysts usable in the process of the invention include for example shaped articles in glass, quartz glass, ceramic, titania, zirconia, alumina, alumosilicates, borates, steatite, magnesium silicate, silica, silicates, carbon, eg. graphite, or mixtures thereof. Alumina is preferred. The support can be porous or nonporous. Suitable shapes are extrudates, tablets, wagon wheels, stars, monoliths, spheres, chippings or rings. Particular preference is given to spheres, tablets and extrudates.

The inert supports typically have BET surface areas of from 0 to 1000 $m^2/g$, preferably from 0.1 to 400 $m^2/g$.

The sols can be applied to the support by various techniques which influence the distribution of the active component. To produce thin shells of the active component for the entire extrudate cross-section, the sol is sprayed onto an indirectly heated support. This is done by presenting the support in a rotatable, heatable pelletizing pan and heating it to temperatures within the range from 80 to 200° C. by means of a hot air blower. As the pan turns, the sol is sprayed onto the support. The turning of the pan ensures that the support particles, for example extrudates or chippings, are thoroughly mixed. On contact with the hot support, liquid in the sol evaporates, leaving the active component behind on the support. This application technique produces catalysts in which the active component is applied on the support in thin layers which are generally less than 5 μm. The particle size of the noble metal agglomerates is generally of the same order of magnitude as in the sol. The catalyst is then dried at a temperature which does not exceed 150° C.

Another technique for applying the active component comprises impregnating the support with a metal sol in accordance with the support's previously determined water absorption capacity, which corresponds essentially to its pore volume. After the support has stopped dripping, it is dried at a temperature which does not exceed 150° C. In catalysts prepared in this way the active component is surprisingly likewise present in a very thin layer. However, when macroporous supports are used, the active component is in this case preferentially present in the externally accessible macropores, while, when the sol is sprayed on, essentially an equal distribution of the active component in micropores and macropores takes place. An essential advantage of the sol impregnation and sol spraying technique is that, after the sol has been applied to the support, the active component is essentially already present in the reduced state. This obviates the need for a reduction of the active component at high temperatures, which generally causes the active component to sinter together and so reduce the catalytic surface area.

The process of the invention involves hydrogenating vinyloxirane, or solutions of vinyloxirane in a solvent which is inert under the reaction conditions, in the presence of the catalysts to be used according to the invention at temperatures of from generally 0 to 200° C., preferably from 10 to 130° C., in particular from 20 to 100° C., and particularly preferably at from 25 to 60° C., at a pressure of from in general 1 to 300 bar, preferably from 1 to 100 bar and particularly preferably from 1 to 50 bar.

The process of the invention can be carried out without a solvent or preferably in the presence of a solvent which is inert under the reaction conditions. Such solvents include for example ethers such as tetrahydrofuran, dioxane, methyl tert-butyl ether, di-n-butyl ether, dimethoxyethane and diisopropyl ether, alcohols such as methanol, ethanol, propanol, isopropanol, n-butanol, isobutanol and tert-butanol, $C_2$–$C_4$-glycols, hydrocarbons such as petroleum ether, benzene, toluene and xylene, and N-alkyllactams such as N-methylpyrrolidone and N-octylpyrrolidone.

The process of the invention can be carried out both continuously and batchwise, in the gas phase or in the liquid phase. A continuous process can be carried out with advantage for example, in tubular reactors in which the catalyst is present as a fixed bed over which the reaction mixture can be passed in the upflow or downflow direction. In a batchwise process, the catalyst can be used for example in suspended form in stirred reactors or preferably in the form of a fixed bed, for example when using loop reactors.

The reaction mixture can be worked up for 1,2-butylene oxide in a conventional manner, for example by distillation.

The vinyloxirane required as starting material can be prepared for example by the process of U.S. Pat. No. 4,897,498 by partial oxidation of 1,3-butadiene over silver catalysts.

1,2-Butylene oxide is used as a motor fuel additive and as a stabilizer of chlorinated hydrocarbons.

PREPARATION OF CATALYSTS

EXAMPLE 1

Preparation of catalyst A (Pd on $Al_2O_3$)

To prepare a stable Pd sol, 1.60 g of 11% strength by weight $Pd(NO_3)_2$ solution and 5 g of polyvinylpyrrolidone were dissolved in 1.17 l of water. 25 ml of 0.8% strength by weight $N_2H_4$ solution were added, and the mixture was stirred at room temperature for ½ hour and then refluxed for 4 h. On cooling, a palladium sol containing 0.15 g of Pd/l was obtained. 400 ml of this sol were diluted to 1 l with 600 ml of water. 100 g of an $Al_2O_3$ support having a BET surface area of 290 $m^2$/g were presented in a heated pelletizing pan and sprayed with the previously prepared dilute sol. The catalyst was dried at 120° C. for 16 h. Thereafter the catalyst contained 0.05% by weight of palladium, based on the supported catalyst.

EXAMPLE 2
Preparation of catalyst B (Pd on $Al_2O_3$)

Example 1 was repeated except that only 267 ml of the undiluted sol were diluted to 1000 ml. 100 g of an $Al_2O_3$ support having a BET surface area of 244 $m^2$/g were presented in the heated pelletizing pan and sprayed with the previously prepared dilute sol. The catalyst was dried at 120° C. for 16 h. Thereafter the catalyst contained 0.035% by weight of palladium, based on the supported catalyst.

EXAMPLE 3
Preparation of catalyst C (Pd on $Al_2O_3$)

To prepare a stable Pd sol, 9.09 g of 11% strength by weight $Pd(NO_3)_2$ solution and 5 g of polyvinylpyrrolidone were dissolved in 990 ml of a 1:1 mixture of ethanol and water. The solution was stirred at room temperature for ½ h and then refluxed for 4 h. On cooling, a palladium sol containing 1 g of Pd/l was obtained. 20 ml of this sol were diluted to 1 l with 980 ml of water. 100 g of an $Al_2O_3$ support having a BET surface area of 244 $m^2$/g were presented in a heated pelletizing pan and sprayed with the previously prepared dilute sol. The catalyst was dried at 120° C. for 16 h. Thereafter the catalyst contained 0.023% by weight of palladium, based on the supported catalyst.

EXAMPLE 4
Preparation of catalyst D (Pd on $Al_2O_3$)

To prepare a stable Pd sol, 1.60 g of 11% strength by weight $Pd(NO_3)_2$ solution and 5 g of polyvinylpyrrolidone were dissolved in 1170 ml of water. 25 ml of 0.8% strength by weight $N_2H_4$ solution were added, and the mixture was stirred at room temperature for ½ hour and then refluxed for 4 h.

On cooling, a palladium sol containing 0.15 g of Pd/l was obtained. 33 ml of this sol were diluted to 1 l with water. 100 g of an $Al_2O_3$ support having a BET surface area of 270 $m^2$/g were presented in a heated pelletizing pan and sprayed with the previously prepared dilute sol. The catalyst was dried at 120° C. for 16 h. Thereafter the catalyst contained 0.005% by weight of palladium, based on the supported catalyst.

EXAMPLE 5
Preparation of catalyst E (Pd on steatite)

To prepare a stable Pd sol, 27.27 g of 11% strength by weight $Pd(NO_3)_2$ solution and 5 g of polyvinylpyrrolidone were dissolved in 990 ml of a 1:1 mixture of ethanol and water. The solution was stirred at room temperature for ½ hour and then refluxed for 4 h. On cooling, a palladium sol containing 3 g of Pd/l was obtained. 17 ml were applied in three impregnating stages (2 times 6 ml and once 5 ml) to 100 g of a steatite support (steatite balls without internal surface area). Between each impregnating step an interval of about 1 h was observed, during which the balls were repeatedly shaken. The catalyst was dried at 120° C. for 16 h. Thereafter the catalyst contained 0.027% by weight of palladium, based on the supported catalyst.

EXAMPLE 6
Preparation of catalyst F (Pd on $SiO_2$)

1.37 g of 11% strength by weight $Pd(NO_3)_2$ solution were mixed with 2.25 l of water, and the solution was mixed with 1.5 g of polyvinylpyrrolidone. To this solution were added 750 ml of ethanol, and the solution was refluxed for 4 h. On cooling, a stable sol was obtained. 400 ml of this sol were diluted to 1 l. The dilute sol was sprayed in a heated pelletizing pan onto 100 g of an $SiO_2$ support having a BET surface area of 136 $m^2$/g. The catalyst was then dried at 120° C. for 16 h. The resulting catalyst had a Pd content of 0.024%.

EXAMPLE 7
Preparation of catalyst G (Re on $Al_2O_3$)

1.127 g of rhenium(V) chloride were dissolved in 700 ml of water with the addition of 1.5 g of polyvinylpyrrolidone. This solution was admixed with 300 ml of ethanol and stirred under reflux for 4 h. On cooling, a stable sol was obtained (0.6 g/l). 83 ml of this sol were diluted to 1 l with water. 100 g of an $Al_2O_3$ support having a BET surface area of 222 $m^2$/g were presented in a heated pelletizing pan and sprayed with the previously prepared dilute sol. The catalyst was dried at 120° C.for 16 h. Thereafter the catalyst contained 0.05% by weight of rhenium, based on the supported catalyst.

EXAMPLE 8
Preparation of catalyst H (Ru on $Al_2O_3$)

1.68 g of ruthenium(III) chloride hydrate were dissolved in 700 ml of water with the addition of 5 g of polyvinylpyrrolidone. This solution was admixed with 300 ml of ethanol and stirred under reflux for 4 h. On cooling, a stable sol was obtained (0.6 g/l). 83 ml of this sol were diluted to 1 l with water. 100 g of the support described in Example 7 were presented in a heated pelletizing pan and sprayed with the previously prepared dilute sol. The catalyst was dried at 120° C. for 16 h. Thereafter, according to analysis, the catalyst contained 0.05% by weight of ruthenium, based on the supported catalyst.

EXAMPLE 9
Preparation of catalyst I (Rh on $Al_2O_3$)

1.73 g of rhodium(III) chloride hydrate were dissolved in 700 ml of water with the addition of 1 g of polyvinylpyrrolidone. This solution was admixed with 300 ml of ethanol and stirred under reflux for 4 h. On cooling, a stable sol was obtained (0.6 g/l). 83 ml of this sol were diluted to 1 l with water. 100 g of the support described in Example 7 were presented in a heated pelletizing pan and sprayed with the previously prepared dilute sol. The catalyst was dried at 120° C. for 16 h. Thereafter the catalyst contained 0.05% by weight of rhodium, based on the supported catalyst.

HYDROGENATION EXAMPLES

EXAMPLE 10

A solution of 2.5 g of vinyloxirane in 22.5 g of tetrahydrofuran was hydrogenated with hydrogen in a 50 ml autoclave at 25° C. and 40 bar for 8 h using 0.5 g of suspended catalyst A. According to gas-chromatographic analysis of the hydrogenation effluent, 90 mol % of 1,2-butylene oxide, 1.0 mol % of n-butyraldehyde and 1.7 mol % of n-butanol were obtained at quantitative vinyloxirane conversion.

EXAMPLES 11 TO 18

2.5 g of vinyloxirane in 22.5 g of tetrahydrofuran were hydrogenated at 40 bar over catalysts B–as described in Example 1. The table which follows shows the hydrogenation conditions, temperature, pressure and reaction time and the gas-chromatographic analysis results of the hydrogenation effluents.

TABLE

| Ex. | Catalyst | Cat. [g] | T [°C.] | Reaction time [h] | VO conversion [%] | Yield [mole] BO | n-BA | n-BuOH |
|---|---|---|---|---|---|---|---|---|
| 11 | B | 1 | 20 | 4 | 100 | 85 | 1 | 3 |
| 12 | C | 1 | 20 | 4 | 100 | 82 | 2 | 3 |
| 13 | D | 1 | 20 | 8 | 100 | 80 | 1 | 4 |
| 14 | E | 1 | 20 | 6 | 100 | 81 | 2 | 6 |
| 15 | F | 0.5 | 25 | 6 | 100 | 83 | 4 | 4 |
| 16 | G | 1 | 20 | 17 | 100 | 74 | 1 | 2 |
| 17 | H | 2 | 20 | 24 | 100 | 74 | 1 | 2 |
| 18 | I | 1 | 20 | 8 | 100 | 83* | 1 | 3 |

VO = vinyloxirane,
BO = 1,2-butylene oxide,
n-BA = n-butyraldehyde,
n-BuOH = n-butanol
Ex. = Example,
Cat. = catalyst
* Space-time yield: 550 kg of BO/kg of Rh * h

We claim:

1. A process for preparing 1,2-butylene oxide by catalytic hydrogenation of vinyloxirane over a heterogeneous catalyst, which comprises using a catalyst prepared by applying at least one element from palladium, platinum, rhodium, rhenium or ruthenium in the form of a sol to an inert support.

2. A process as claimed in claim 1, wherein the catalyst used comprises palladium on alumina.

3. A process as claimed in claim 1, wherein the sol is prepared by reducing a salt of an element of groups 7 to 10 of the Periodic Table in the presence of polyvinylpyrrolidone.

4. A process as claimed in claim 3, wherein hydrazine or ethanol is used as reducing agent.

* * * * *